United States Patent [19]

Young et al.

[11] Patent Number: 4,698,443
[45] Date of Patent: Oct. 6, 1987

[54] BIURET PURIFICATION

[75] Inventors: Donald C. Young, Fullerton; James A. Green, II, Chino, both of Calif.

[73] Assignee: Union Oil Company of California, Los Angeles, Calif.

[21] Appl. No.: 753,693

[22] Filed: Jul. 10, 1985

[51] Int. Cl.⁴ .................. C07C 127/24; C07C 126/08
[52] U.S. Cl. ........................................ 564/38; 564/73
[58] Field of Search .................................. 564/38, 73

[56] References Cited

U.S. PATENT DOCUMENTS

| | | | |
|---|---|---|---|
| 3,150,177 | 9/1964 | Kluge | 564/38 |
| 3,184,508 | 5/1965 | Kaasenbrood | 564/38 |
| 3,185,731 | 5/1965 | Kaasenbrood | 260/555 |
| 3,846,298 | 11/1974 | Plura | 210/33 |
| 3,903,158 | 9/1975 | Fuentes et al. | 260/555 |
| 4,345,099 | 8/1982 | Young et al. | 564/63 |

FOREIGN PATENT DOCUMENTS 1156099  6/1969  United Kingdom .

OTHER PUBLICATIONS

Kucheryavyi et al., Chem. Abs. 68(6):24698p.
Kirk–Othmer Encyclopedia of Chemical Technology, 2nd Edition, vol. 4, pp. 149–151 (1963).
Takahashi & Yoshida, Determination of Biuret in Urea by Ion Exchange Resins, Soil and Plant Food, vol. 3, Jan. 1958, pp. 142–144.
Mithyantha et al., Biuret and Crop Production, Fertilizer News, 1977, pp. 13–18.
Donald C. Young and James A. Green, II, Application Ser. Nos. 567,271 for Methods for Removing Biuret from Urea by Ion Exchange; 567,099 for Ion Exchange Methods for Removing Biuret from Urea; and 567,047 for Method for Removing Biuret from Urea, all filed Dec. 30, 1983.
James A. Green, II and Donald C. Young, U.S. Application Ser. No. 732,175 filed May 7, 1985, for Manufacture of Biuret.
Donald C. Young and James E. Green, II, U.S. Application Ser. No. 753,692 filed Jul. 10, 1985 for Methods for Removing Biuret from Urea by Adsorption.
Endo, et al., Chem. Abst. 90:143400z.
James A. Green, II, and Donald C. Young, U.S. Application Ser. No. 725,304, filed Apr. 19, 1985 for Methods for Purifying Biuret.

Primary Examiner—Charles F. Warren
Assistant Examiner—Carolyn S. Greason
Attorney, Agent, or Firm—Michael H. Laird; Greg Wirzbicki; Dean Sandford

[57] ABSTRACT

Purified biuret is recovered from mixtures containing biuret and higher molecular weight urea condensation products by contacting melts or solutions of such mixtures with a polar adsorbent and extracting biuret from the adsorbent with a polar desorbent. The useful biuret-containing mixtures also may contain urea. These methods are capable of recovering biuret of 99.9 percent plus purity from mixture containing higher molecular weight urea condensations products such as triuret, melamine, ammelide, and others. The biuret-containing desorbent can be recycled into contact with biuret-containing adsorbents to increase its biuret concentration, concentrated by evaporation of otherwise, and/or treated to crystallize biuret. An integrated process is provided which involves pyrolyzing urea to form biuret and higher molecular weight condensation products and selectively recovering biuret from the resulting pyrolyzed urea as described.

26 Claims, No Drawings

BIURET PURIFICATION

BACKGROUND OF THE INVENTION

1. Field of the Invention

This invention relates to methods for producing biuret, and in particular, it relates to methods for recovering purified biuret from mixtures of biuret and higher molecular weight urea condensation products.

2. Description of the Art

Biuret is widely used in commerce as a precursor for pharmaceuticals, herbicides, and other compounds, as an analytical reagent, and as a ruminant feed supplement. All of these utilities benefit from (if not require) the use of relatively pure biuret.

While biuret can be produced by several chemical methods, it is typically obtained by pyrolyzing urea at a temperature of at least 130° C. and for a period of time sufficient to convert at least a portion of the urea to biuret. An illustrative urea pyrolysis process is discussed by Shipley and Watchorn in British Pat. No. 1,156,099. Unfortunately, as disclosed by Shipley et al., a portion of the urea and biuret are often converted, during pyrolysis, to higher molecular weight urea condensation products such as triuret, cyanuric acid, ammelide, melamine, ammonium cyanurate, methylene diurea, and/or other compounds. Furthermore, a large part of the urea that is manufactured as solid prills is treated at temperatures, during the manufacturing process, that result in some conversion of urea to biuret and higher molecular weight compounds. While the biuret concentration in prilled ureas is typically low, e.g., 0.5 to 3 weight percent, the amount of biuret contained in such products is substantial due to the large volume of prilled urea manufactured annually. The commercial biuret-containing prilled ureas often also contain higher molecular weight urea condensation products such as those mentioned above.

Many of the higher molecular weight condensation products appear to form by the reaction of urea with itself or with previously formed condensation products, or by reactions of, or between, previously formed condensation products. Others, such as methylene diurea, appear to form by the reaction of urea and/or condensation products with additives or other impurities such as formaldehyde which is sometimes employed as a urea anti-caking agent. Regardless of their origin, one or more of such impurities are known to exist in biuret obtained from urea by presently available methods as discussed by Shipley et al., supra, and Kassenbrood in U.S. Pat. No. 3,185,731.

While urea pyrolysis and prilled urea manufacture afford an ample supply of biuret, the major utilities for biuret benefit from the use of that compound in relatively pure form. For instance, analytical procedures and pharmaceutical and herbicide manufacturing practices involving the use of biuret are most often unacceptably complicated by the presence of higher molecular weight condensation products, and the biuret dosage rate which can be employed in ruminant feed supplements is often limited by the toxicity of such impurities.

Methods presently employed to recover pure biuret from mixtures of urea, biuret and higher molecular weight condensation products involve expensive, time consuming, repeated low temperature recrystallization from aqueous solution. The expense involved in such methods obviously increases the cost of pure biuret derived from such sources and limits its application. For instance, ruminant feed supplement manufacturers generally choose to use relatively impure, less expensive biuret at dosage rates which are sufficiently low to avoid the toxic effects of impurities.

Several authors have disclosed that biuret can be removed from urea by contact with the hydroxide ion form of an anion exchanger. For instance Fuentes et al., U.S. Pat. No. 3,903,158 and Takahashi et al., "Determination of Biuret in Urea by Ion Exchange Resins," Soil and Plant Food, Vol. 3, No. 3, Jan. 1958, pages 142–144, disclose that biuret can be removed from aqueous solutions by ion exchange. Neither Fuentes et al. nor Takahashi et al. mention the presence of any other impurities or the possibility that impurity-free biuret can be recovered from mixtures containing higher molecular weight urea condensation products. In fact, Takahashi et al. disclose that "usually, urea for agriculture does not contain nitrogen compounds other than biuret." (Ibid., page 144). While that is often the case, some ureas, in particular those formed by pyrolyzing urea at temperatures above 130° C. for any significant period of time, contain a significant proportion of urea condensation products of higher molecular weight than biuret, some of which are toxic, and all of which can impair product utility.

The use of strongly basic anion exchangers to remove biuret from urea as disclosed by Fuentes et al. and Takahashi et al., supra, suffers from several further disadvantages. Strongly basic anion exchangers such as Amberlite IRA-400 cost in the range of about $50 to about $150 per cubic foot. The strongly caustic or acidic solutions used to regenerate the exchangers are also relatively expensive. Since, according to the literature, the biuret is relatively strongly held by the anion exchanger (a feature which would be beneficial from the standpoint of assuring adequate removal of biuret from the urea solution), the art suggests that relatively severe regeneration conditions are required to efficiently remove the biuret from the deactivated anion exchanger. Obviously, the cost of anion exchanger regeneration, the cost of constructing, maintaining and operating a system capable of removing biuret from a certain quantity of urea solution, and the expense of the anion exchanger required in the process, all increase as the frequency and/or severity of regeneration increases. Thus, the requirement for frequent and/or more severe regeneration increases regenerant costs and the amount of anion exchanger and the size of the operating facility required to treat a given amount of urea solution. The strong base ion exchangers and caustic regenerants used by Fuentes et al. and Takahashi et al. both decompose biuret, and the composition of base by regeneration and by reaction with biuret further increases operating cost.

SUMMARY OF THE INVENTION

It has now been discovered that biuret can be selectively, efficiently and economically recovered from mixtures of biuret and higher molecular weight urea condensation products by contacting a melt or solution of such mixtures with a polar adsorbent. More specifically, purified biuret is produced by contacting melts or solutions containing biuret and higher molecular weight urea condensation products with a polar adsorbent under conditions sufficient to retain at least a portion of the biuret on the adsorbent, and extracting at least a portion of the retained biuret from the adsorbent with a polar desorbent under conditions sufficient to obtain a biuret-containing extract which contains a lower relative proportion of the higher molecular weight urea condensation products. The preferred method of the invention further provides for the relatively selective recovery of biuret from mixtures which contain substantial amounts of urea.

While the desorbent can be either acidic, neutral or alkaline, highly alkaline aqueous desorbents are desirably neutralized and/or cooled before use to minimize or eliminate biuret loss by hydrolysis. Extracts which have higher biuret concentrations can be obtained by performing the desorption at elevated temperatures, e.g. of at least about 30° C., and/or by recycling the biuret-containing extract (desorbent) into contact with one or more biuret-containing adsorbents. Pure biuret can be obtained, for instance, by chilling the extract to a temperature sufficient to crystallize biuret from the solution.

These methods provide for the efficient and economical recovery of biuret from mixtures of biuret and higher molecular weight urea condensation products without the expense or complexity of repeated, low temperature recrystallization (which is otherwise required to separate biuret from higher molecular weight urea condensation products). These methods also eliminate the need for costly ion exchangers and the expense and complexity of exchanger activation and regeneration. Such ion exchange processes are discussed in our copending application Ser. No. 725,304 filed Apr. 19, 1985 for "Methods for Purifying Biuret," the disclosure of which is incorporated herein by reference in its entirety. These methods also reduce or eliminate biuret loss by reaction with the caustic regenerants and/or the basic anion exchangers of Fuentes et al. and Takahashi et al., and they reduce or eliminate the consumption of chemical reagents such as the caustic regenerants of Fuentes et al. and Takahashi et al.

While the fate of the higher molecular weight impurities is not known with certainty, one or more of such impurities may be decomposed by contact with the polar adsorbent while others may pass through the adsorbent ahead of the biuret. Whatever the exact chemical mechanism, the methods of this invention can be employed to recover biuret of purity as high as 99.9 plus weight percent from mixtures of biuret and higher molecular weight urea condensation products in the presence or absence of urea. These methods have the further advantage that they enable the recovery of purified biuret as a by-product of urea purification as described in our co-pending application Ser. No. 753,692 for METHODS FOR REMOVING BIURET FROM UREA BY ADSORPTION filed concurrently with this application, the disclosure of which is incorporated herein by reference in its entirety. They also enable the essentially complete recovery of purified biuret from such impurity-containing mixtures without significant biuret loss due to hydrolysis or other chemical reactions.

DETAILED DESCRIPTION OF THE INVENTION

One embodiment of this invention involves selectively removing biuret from a mixture of biuret and higher molecular weight urea condensation products, in the presence or absence of urea, by contacting a melt or solution of the mixture with a polar adsorbent under conditions sufficient to retain at least a portion of the biuret on the adsorbent and subsquentially removing the retained biuret by contact with a polar desorbent. Although acidic, neutral and alkaline desorbents can be employed, the strongly alkaline aqueous desorbents are preferably neutralized to about pH 7 or less following the biuret desorption step to prevent biuret hydrolysis.

These procedures are capable of producing biuret of 99.9 percent plus purity from mixtures which contain substantial proportions of higher molecular weight urea condensation products such as triuret, melamine, etc. Biuret concentration in the extract can be increased by employing higher extraction temperatures, e.g. 30° C. or higher, and/or by recycling the biuret-containing desorbent into contact with one or more biuret-containing absorbents to extract additional biuret. The biuret-containing extract can be employed as is, can be concentrated further by evaporation, or can be employed to produce pure, solid biuret, e.g. by low temperature crystallization.

Another embodiment provides an integrated process for producing biuret from urea in which urea is pyrolyzed at a temperature of about 130° C. or higher and for a period of time sufficient to convert at least a portion of the urea to biuret and higher molecular weight urea condensation products, after which biuret is recovered as described above. When all of the urea has not been pyrolyzed, residual urea of reduced biuret content can be recovered and employed to produce additional quantities of biuret by pyrolysis.

The biuret-containing mixtures useful in this invention typically contain higher molecular weight urea condensation products, such as triuret, cyanuric acid, ammonium cyanurate, methylene diurea, and cyclic polyamides such as melamine and ammelide. Such mixtures can either be employed as manufactured commercially or they can be pretreated (by exposure to elevated temperatures) to increase biuret content. While aqueous solutions are the most common, feed solutions in polar organic solvents can also be employed. Illustrative organic solvents include aldehydes such as formaldehyde, propionaldehyde, etc., ketones such as methylethylketone, alcohols such as isopropanol, organic acids such as acetic, butyric, propionic, etc., amines, amides, thiols, and other polar compounds and combinations of such compounds.

Illustrative useful solutions include those obtained from urea manufacturing plants prior to dehydration, solutions formed by dissolving impure biuret or biuret-containing urea in water, and impure biuret solutions from which some or all of the urea has been separated by crystallization or otherwise as discussed, for instance, in British Pat. No. 1,156,099 and U.S. Pat. No. 3,185,731, the disclosures of which are incorporated herein by reference in their entireties. Illustrative useful melts include dehydrated urea melts obtained from urea manufacturing facilities, melts formed by heating biuret containing ureas to temperatures above their melting points, and melts obtained by melting relatively high biuret content solids from which a major portion of the urea has been removed by crystallization or otherwise as discussed, for instance, in British Pat. No. 1,156,099 and U.S. Pat. No. 3,185,731.

Many commercially available prilled ureas, which are typically formed by prilling urea from a melt at a temperature of about 130° C. or higher, contain about 0.5 to about 3 weight percent biuret based on urea, and they also may contain higher molecular weight urea condensation products. The impurities constitute at least about 5, generally at least about 10, and most often about 5 to about 50 weight percent of the composition based on biuret. Triuret usually accounts for approximately one half of the impurity content of impure prilled urea.

Ureas which have been intentionally pyrolyzed to form biuret typically contain substantially higher proportions of biuret and higher molecular weight impurities. Pyrolysis is usually effected by treatment at a temperature of at least about 135° C., generally about 135° to about 180° C., for a period of time sufficient to convert at least a portion of the urea to biuret. Contact times of at least about 2 minutes are usually employed, although significant urea conversion usually requires treatment for about 5 minutes to about 5 hours. The rate of urea conversion increases with temperature; thus, the contact time required to achieve a certain degree of urea pyrolysis decreases as treatment temperature is increased.

While all of the urea can be pyrolyzed to biuret and higher molecular weight urea condensation products, higher conversions require the use of higher temperatures and/or longer contact times which result in higher impurity/biuret ratios and the loss of biuret product. Biuret loss under severe pyrolysis conditions is due, at least in part, to the pyrolysis of biuret to higher molecular weight compounds. Thus, the urea is typically only partially pyrolyzed under conditions sufficient to yield at least about 5 weight percent, generally about 10 to about 50 weight percent biuret based on urea. The higher biuret concentrations are usually associated with higher impurity/biuret ratios due to the more severe pyrolysis required to achieve such biuret levels. Further explanation of the relationship of pyrolysis time and temperature and of impurity concentration is given in "Urea, Its Properties and Manufacture," George C. Tsei-Yu-Chao, 1967, Library of Congress Catalog Card number Ai-11254, published by Chao's Institute, West Covina, California particularly on pages 119-123, the disclosure of which is incorporated herein by reference in its entirety.

Thus, rather than aiming to form pure biuret by pyrolysis of urea, the present invention seeks to selectively recover essentially pure biuret from mixtures containing biuret and higher molecular weight urea condensation products. Typically, such solutions contain about 1 to about 80 weight percent, preferably about 2 to about 70 weight percent solute including biuret and higher molecular weight urea condensation products in the presence or absence of urea. Maximum solution concentration is usually determined by solution temperature which can range from 10° C. to about 100° C. At temperatures above 70° C. urea decomposition by hydrolysis becomes more rapid. Accordingly, aqueous solutions which contain substantial urea are preferably maintained at about 70° C. or less.

Urea has a solubility of approximately 80 weight percent in water at 70° C. and biuret will dissolve in water to a level of approximately 20 weight percent at the same temperature. However, biuret is more soluble in urea solutions. Thus, higher biuret concentrations can be achieved in the presence of substantial amounts of dissolved urea.

While the aqueous solutions can be employed as prepared, they usually contain sufficient ammonia to produce a relatively basic aqueous solution. Although this condition can be tolerated, pH levels of about 12 and above promote urea and biuret hydrolysis and are preferably avoided. Accordingly, the aqueous feed solutions will usually be relatively non-alkaline and will generally have a pH below 12, usually about 10 or less, preferably about 6 or less, and most preferably about 3 to about 6. Alkaline solutions can be neutralized and/or buffered to obtain the desired pH by adding any suitable organic or inorganic acid such as sulfuric, hydrochloric, nitric, acetic, etc., or buffering agents such as ammonium polyphosphate. Relatively acidic solutions are particularly preferred for use at higher temperatures and/or longer contact times.

The useful adsorbents include all polar adsorbents including natural and synthetic, amorphous and crystalline, organic and inorganic, acidic, neutral and basic adsorbent materials. They are distinguished from ion exchangers such as those discussed by Fuentes et al. and Takahashi et al., supra, in that they typically have ion exchange capacities of less than about 0.1, generally less than 0.05 milliequivalents of exchange capacity per ml. of adsorbent. Ion exchangers, including ion exchange resins, aluminosilicates and other inorganic oxides typically have exchange capacities of 0.13 to 2.0 meq./ml. The term "adsorbents" is used herein in its conventional sense to connote solid materials which retain one or more components of gases or solutions predominantly, if not exclusively, by mutual physical-chemical attraction rather than by the literal exchange of ions which is the predominant mechanism of ion exchange processes. Typically, the adsorbent's biuret adsorption capacity is at least about twice its ion exchange capacity (if any).

Illustrative inorganic adsorbents include natural and synthetic amorphous and crystalline oxides, such as silica, oxides of metals such as beryllium, magnesium, calcium, boron, aluminum, gallium, etc., e.g., alumina, magnesia, beryllia, magnesium silicates, magnesium hydrogen silicates, calcium silicates, aluminosilicates and mixtures or coprecipitates of such oxides. In addition, suitable adsorbents can be obtained by impregnating a porous substrate with one or more of such polar adsorbents, and the polar adsorbent or impregnated adsorbent, as the case may be, can be acid or caustic treated or calcined to modify its physical or chemical properties. When calcination is employed, however, relatively low temperatures are presently preferred since extreme temperatures, e.g. 800° C. and above, can dehydroxylate adsorbents and convert them to relatively non-polar materials. Examples of suitable polar inorganic adsorbents include silica gel, silica sols, boehmite alumina, Florisil, Magnesol, Silicalite, silica-beryllia cogels, clays such as montmorillonite, halloysite, kaolinite, diatomaceous earth, celite, kiesselguhr, organo-clays such as derivatives of montmorillonite which have been exchanged with quaternary ammonium ions to form bentones, etc.

Illustrative organic adsorbents include oxidized carbons, natural and synthetic polymers which contain pendant polar groups such as hydroxyl, carboxyl, sulfate, sulfite, amino, amido, thiol, thio, oxy, phosphate, phosphite, etc. including homo-, co-, graft, and substituted (chemically modified) polymers. Specific organic adsorbents include charcoal which has been oxidized at temperature of less than about 400° C., untreated or acid and/or caustic-treated cellulosic matter, e.g., cotton, paper, sawdust, dehydrated plant matter, and other cellulosic material, polyacrylates such as polymers of acrylic acid, ethylhexylacrylate, hydroxyethylacrylate, methacrylic acid, ethylmethacrylate, and the like, phenolics such as phenol-formaldehyde polymers, polyethylene thiols, polycaprolactam, etc. Particularly practical organic adsorbents include cellulose and the acrylate polymers due, primarily, to their availability and relatively low cost.

Suitable adsorbents are commercially available from several manufacturers such as Bio-Rad Laboratories of Richmond, Calif. which markets a silica adsorbent as Bio-Sil A ®, neutral, basic and acidic alumina as grades AG-7, AG-10, and AG-4, respectively, and a polar acrylic ester adsorbent as Bio-Beads SM-7 ®.

In addition to the above noted chemical characteristics of suitable adsorbents, they should contain sufficient surface area to present adequate surface for the adsorption of biuret from the urea melts or solutions. Typically, such adsorbents will have surface areas of at least about 10, and generally at least about 50 square meters per gram.

All of the process steps, including the adsorption of biuret from the feed solution and the removal of biuret from the resulting biuret-containing adsorbent, can be performed either by batch contacting or by continuous plug flow contacting in which the feed and desorbent are passed through the adsorbent retained in a relatively fixed bed. Plug flow systems can be operated either downflow or upflow, although downflow systems are generally preferred.

Each increment of the biuret-containing feed is usually contacted with the adsorbent for at least about 30 seconds, preferably at least about one minute, most preferably at least about 5 minutes, and generally about one minute to about one hour. Contact times of about 5 to about 30 minutes are usually adequate to effect the desired degree of biuret adsorption. Such contact times correspond to flow rates of about 2 bed volumes per minute or less, usually about 1 bed volume per minute or less, preferably about 0.2 bed volumes per minute or less, and most preferably about 0.02 to about 1 bed volume per minute.

Contact of the adsorbent with the biuret-containing feed is usually, although not necessarily, continued until the capacity of the adsorbent is depleted. Depletion of adsorbent capacity is indicated in the preferred, continuous, fixed bed systems by biuret breakthrough, which occurs when a detectable quantity of biuret is present in the solution mixture recovered from the adsorbent. However, the biuret adsorption step can be continued past the point of biuret breakthrough if desired.

The biuret-containing feed can be contacted with the adsorbent at any temperature above the freezing point and below the upper temperature limit (e.g., boiling or decomposition point) of the melt or solution. Anhydrous urea melts at 132.7° C. and pure biuret decomposes, before melting, at 193° C. However, minor amounts of water, e.g. 0.5 to about 5 weight percent, present in many urea melts significantly reduce the urea melting point, e.g. to 125° C. and less. Furthermore, biuret is very soluble in urea melts and solutions and thus is generally contacted with the adsorbent in admixture with at least minor amounts of urea, e.g. at least about 5 weight percent urea based on total dry weight of the feed mixture. In view of these considerations, the biuret-containing melts, when employed, are usually contacted with the adsorbent at a temperature of at least about 120° C., typically about 120° to 135° C. Temperatures only slightly above the melting point of the mixture are sufficient. When solutions are employed, the solution generally will be contacted with the exchanger at a temperature of about 0° to about 100° C., generally about 25° to about 70° C. and preferably about 30° to 70° C. depending, of course, on solvent boiling and freezing points. While higher temperatures can be employed, urea decomposition rate in aqueous systems (to $CO_2$ and ammonia) increases rapidly at temperatures above 70° C., and such temperatures are preferably avoided in the presence of water. Higher temperatures increase solubility and biuret adsorption and thereby reduce the time required to adsorb a given amount of biuret. They also markedly increase urea and biuret hydrolysis rates under alkaline aqueous conditions. Therefore, it is preferable to acidify aqueous feed solutions at least to about neutrality and preferably to a pH below 7 when higher solution contacting temperatures are employed.

After the biuret adsorption step, excess feed solution is removed from the adsorbent, and the biuret-containing adsorbent is contacted with a desorbent under conditions sufficient to form a biuret-containing extract containing a reduced proportion, if any, of higher molecular weight urea condensation products. The desorbent can be contacted with the exchanger by either batch or column operations as described above with regard to the biuret adsorption step.

It is sometimes desirable, although not essential, to backwash the adsorbent to remove foreign matter, to flush remaining feed solution from the adsorbent and/or to "reclassify" the bed of adsorbent particles. Backwashing is usually effected by passing water rapidly upwardly through the bed to expand the bed by, e.g., 50 percent. However, substantial backwashing of the biuret-containing adsorbent at this point in the operation is not preferred since even neutral water is capable of removing biuret from the adsorbent. Thus, biuret recovery can be maximized by deferring substantial backwashing until the biuret recovery step is completed as described hereinafter. The adsorbent can be washed with a minor amount of water, e.g. one bed volume or less, and/or can be blown free of residual feed solution with a pressurized gas such as air, nitrogen, etc., to reduce or prevent contamination of the biuret product with the feed and other impurities.

The useful desorbents are polar, organic or inorganic, acidic, neutral or alkaline materials in which biuret is soluble under contacting conditions. Although desorbents which are less polar than biuret can be employed for this purpose, preferred desorbents are more polar than biuret since they more readily displace biuret from the adsorbent. Illustrative desorbents include water, acidic or basic aqueous media such as aqueous sulfuric acid, hydrochloric acid, nitric acid, sodium hydroxide, calcium hydroxide, ammonium hydroxide, organic desorbents such as aldehydes including formaldehyde, propionaldehyde, etc., ketones such as methylethylketone, alcohols such as isopropanol, organic acids such as acetic, butyric, propionic, etc., amines, amides, thiols, and other polar compounds and combinations of such compounds. Aqueous neutral, basic or acidic desorbents are presently preferred for economy and due to the high solubility of biuret in such desorbents.

The preferred aqueous desorbents can be either acidic, neutral or alkaline, although substantially non-alkaline desorbents are presently preferred due to the tendency of alkaline aqueous media to hydrolyze biuret, particularly at elevated temperatures. Illustrative aqueous desorbents include water, ammonium hydroxide solution, e.g.(1 N $NH_4OH$), and caustic, e.g., up to 8 percent sodium hydroxide. Deionized water or distilled water are presently preferred, and these can be acidified if desired.

At least slight acidification of the aqueous desorbents, either before contacting with the adsorbent or subsequent to the biuret removal step, is presently preferred, particularly when operating at higher temperatures. Acidification minimizes the loss of biuret by hydrolysis. Thus, the most preferred aqueous desorbents usually have a pH of about 7 or less, preferably below about 6, and generally within the range of about 1 to about 7. Any organic or inorganic acid can be employed to effect the desired degree of acidification.

The biuret-containing adsorbent is contacted with a sufficient volume of desorbent for a sufficient period of time to remove a substantial proportion of the biuret from the adsorbent. Typically, at least one volume of desorbent will be employed per volume of adsorbent, although much higher desorbent volumes can be used. Thus, desorbent volume will usually range from about 1 to about 100 volumes per volume of desorbent, although most operations will involve the use of about 1 to about 10 volumes of desorbent per volume of adsorbent. Shorter contact times are required to achieve the same degree of biuret removal at higher temperatures due to increased biuret solubility and high desorption rates. Thus, contact time can be varied depending on the temperature employed. Typically, contact times for the desorption step will be at least about 10 minutes to about 5 hours. Such contact times, in fixed bed systems, correspond to desorbent flow rates of less than about 10, preferably less than about 5 volumes of desorbent per volume of adsorbent per hour (V/V/hr.).

Desorption temperature should be sufficiently low to prevent substantial biuret hydrolysis when alkaline aqueous desorbents are employed. Thus, extraction temperatures are generally below 40° C. and preferably below 30° C. when basic aqueous desorbents are used. Biuret hydrolysis in alkaline aqueous systems is relatively slow at 24° C.

Organic and neutral or acidic aqueous desorbents can be employed at higher temperatures without significant biuret hydrolysis, and higher temperatures are presently preferred due to the higher solubility of biuret at such temperatures. For instance, biuret solubility in pure water is 0.53 weight percent at 0° C., 2 percent at 25° C., 7 percent at 50° C., 20 percent at 75° C., and almost 48 percent at 100° C. Elevated temperatures also increase biuret desorption rate from the adsorbent. Accordingly, neutral or acidic aqueous desorbents and elevated temperatures of at least about 25° C., generally about 25° to about 100° C., and preferably about 30° to about 100° C. are employed.

Desorbent-adsorbent contacting can be by either batch or co-current or countercurrent fixed bed procedures or combinations of these. Furthermore, single or multiple contacts with the same or different desorbent can be employed in both batch and fixed bed systems. In a presently preferred embodiment, the extract recovered from the adsorbent is recycled into contact either with the same adsorbent or with another biuret-containing adsorbent to increase the biuret concentration in the extract. Also, the first portion of extract (a fraction of an adsorbent volume up to several volumes) recovered from the adsorbent, which typically has a higher biuret content than subsequent portions of extract, can be recovered as product and/or processed by crystallization, evaporation, etc., and subsequent portions, typically of lower biuret content, can be recycled.

The desorbent can be recycled up to 100 times depending on the biuret concentration desired, contact time between the adsorbent and each volume of desorbent during each cycle, temperature, and the quantity of biuret on each adsorbent contacted. Usually, however, the desorbent or a portion thereof, will be recycled 1 to about 20 times unless biuret is recovered from the desorbent. If biuret is removed by crystallization or otherwise, the desorbent can be recycled indefinitely.

It is sometimes preferable to obtain an extract having a relatively high biuret content, e.g. of 4 weight percent or more, for instance when biuret is to be recovered from the extract by crystallization or otherwise. Such high biuret concentrations can be achieved by the use of longer contact times, lower volumes of desorbent per volume of adsorbent, higher adsorbent biuret loadings, higher contacting temperatures, higher recycle ratios, or combinations of two or more of these procedures.

The recovered biuret-containing extract will generally contain at least about 0.1 weight percent, typically about 0.1 to about 50 weight percent, and preferably about 2 to about 50 weight percent biuret. Biuret concentrations of at least about 4 weight percent, particularly at least about 10 weight percent, are preferred for the production of more concentrated solutions, e.g. by evaporation, or for the production of solid biuret by crystallization or otherwise.

Following recovery of the biuret-containing extract from the adsorbent, the adsorbent can be employed to remove biuret from additional quantities of the impure biuret-containing feed mixture with or without further regeneration. Occasionally, however, adsorbent activity may become diminished due to the adsorption of strongly adsorbed compounds such as alkali and alkaline earth metal carbonates and sulfates which may not be completely desorbed during the desorption step. Adsorbent capacity can also be depleted by adsorption of impurities from the biuret-containing feed which are not desorbed during the desorption step. For these reasons, it is preferable, when adsorbent activity declines, to further regenerate the adsorbent with a strongly polar regenerant such as aqueous, caustic, and/or acid solutions. Regeneration with strong caustic, e.g. 2 to about 8 weight percent sodium hydroxide solution, or acids such as 2 weight percent aqueous hydrochloric and/or sulfuric acids, is usually sufficient to restore most if not all of the adsorbent activity. Adsorbent-regenerant contacting can be carried out by batch or continuous operations as described above with regard to the biuret adsorption step. Typically, such regeneration involves contacting the adsorbent with at least one volume of regenerant per volume of adsorbent for at least about 1 minute, typically about 1 to about 20 minutes, sufficient to displace adsorbed compounds and restore the active polarity of the adsorbent. In the alternative, the inorganic adsorbents and carbon can be reactivated by washing them free of readily elutable materials (caustic and/or acid washing can also be employed in this step) followed by heating in an oxidizing atmosphere such as air to a temperature sufficient to restore the adsorbent's activity. Activation temperatures involved in such procedures are typically at least about 200° C., often at least about 400° C., and should not exceed the deactivation or sintering temperatures of the adsorbent and, therefore, are generally kept below 800° C.

Extracts prepared in accordance with this invention contain substantially lower proportions of the higher molecular weight urea condensation products present in the feed. Typically, the proportion of higher molecular weight impurities present in the extract will be less than one half, preferably less than one tenth the concentration of those impurities in the feed solution based on biuret. Thus, biuret of greater than 95 percent purity can be obtained by these methods. When care is taken to avoid contamination of the extract with the residual feed mixture on the adsorbent, biuret purity of at least about 99 percent and even 99.9 percent plus can be achieved.

The recovered biuret-containing extract can be employed as is as a herbicide, chemical precursor, animal feed supplement, or for other utilities. Alternatively, a proportion or all of the solvent (desorbent) in the extract can be evaporated to obtain either crystalline biuret or a concentrated biuret solution. When elevated temperature evaporation is employed with aqueous extracts, care should be taken to assure that the extract is approximately pH neutral or acidic prior to exposure to elevated temperatures to avoid biuret loss.

In a particularly preferred embodiment, the biuret concentration in the extract is increased either by recycling or otherwise as described above or by evaporation to obtain a biuret concentration of at least about 4 weight percent, preferably at least about 10 weight percent, after which the concentrated solution is chilled to a temperature, e.g. about 0° C., sufficient to crystallize biuret from the solution. The crystalline biuret can be recovered by any suitable solid-liquid separation means such as filtration, decanting, etc.

The invention is further described by the following examples which are illustrative of specific modes of practicing the invention and are not intended as limiting the scope of the invention as defined by the appended claims.

EXAMPLE 1

Biuret can be selectively recovered from an aqueous solution containing approximately 50 weight percent urea, 2 weight percent biuret based on urea and 10 weight percent of higher molecular weight urea condensation products based on biuret, including methylene diurea and triuret, by passing the solution downwardly at a rate of 25 ml./min. through a glass column packed with 250 ml. loosely packed cotton fiber at a temperature of approximately 25° C. until biuret is detected in the column effluent. The feed to the column can then be discontinued and urea solution remaining in the adsorbent bed can be removed by draining and passing humidified air downwardly through the column. Adsorbed biuret can then be recovered by contacting the cotton adsorbent with 2-bed volumes of 1 percent sodium hydroxide solution passed downwardly through the column at a rate of 25 ml. per minute at a temperature of 20° C. The described adsorption-desorption steps can then be repeated.

EXAMPLE 2

Biuret can be selectively recovered from the impure urea solution described in Example 1 by passing the solution downwardly through the glass column described in Example 1 packed to a volume of 250 ml. with BIO-Beads SM7 ®, an acrylic ester macroporous polymer material available from BIO-RAD Laboratories, Inc. of Richmond, California. The urea solution can be passed downwardly through the bed at a rate of 25 ml. per minute until biuret breakthrough is observed. Recovery of residual feed solution from the bed and desorption of biuret can be carried out as described in Example 1.

While particular embodiments of this invention have been described, it will be understood, of course, that the invention is not limited thereto since many obvious modifications can be made, and it is intended to include within this invention any such modifications as will fall within the spirit and scope of the appended claims.

We claim:

1. A method for recovering purified biuret from a mixture which comprises biuret and higher molecular weight urea condensation products which method comprises (a) contacting a solution or melt of said mixture with a polar adsorbent under conditions sufficient to retain at least a portion of said biuret on said adsorbent and (b) contacting the resulting biuret-containing adsorbent with a polar desorbent in which said biuret is soluble under conditions sufficient to form a biuret-containing extract.

2. The method defined in claim 1 wherein said higher molecular weight urea condensation products comprise a member selected from the group consisting of triuret, melamine, cyanuric acid, ammonium cyanurate, ammelide, methylene diurea, and combinations thereof, and said higher molecular weight urea condensation products constitute less than 5 weight percent of said extract based on biuret.

3. The method defined in claim 2 wherein said higher molecular weight urea condensation products comprise about one weight percent or less of said extract based on biuret.

4. The method defined in claim 1 which further comprises the step of contacting said biuret-containing extract with a biuret-containing adsorbent under conditions sufficient to increase the biuret concentration of said extract.

5. The method defined in claim 1 wherein said desorbent is aqueous and is contacted with said biuret-containing adsorbent at a pH below about 7.

6. The method defined in claim 5 wherein said pH is below about 6.

7. The method defined in claim 1 which further comprises the step of reducing the pH of said biuret-containing extract to less than 7.

8. The method defined in claim 1 wherein said desorbent is contacted with said biuret-containing adsorbent at a temperature of at least about 30° C.

9. The method defined in claim 1 wherein said desorbent is contacted with said biuret-containing adsorbent at a temperature of at least about 50° C.

10. The method defined in claim 1 wherein said desorbent is aqueous, has a pH below 7, and is contacted with said biuret-containing adsorbent at a temperature of at least about 30° C.

11. The method defined in claim 1 wherein said higher molecular weight urea condensation products comprise a member selected from the group consisting of triuret, melamine, cyanuric acid, ammonium cyanurate, ammelide, methylene diurea and combinations thereof, said desorbent is aqueous, has a pH below 7, and is contacted with said biuret-containing desorbent at a temperature of at least about 50° C., and said higher molecular weight condensation products constitute about 5 weight percent or less of said biuret-containing extract.

12. The method defined in claim 11 wherein at least a portion of said biuret is recovered from said extract.

13. The method defined in claim 11 wherein said biuret-containing extract is cooled to a temperature sufficient to crystallize at least a portion of said biuret from said extract.

14. The method defined in claim 1 wherein said mixture comprises at least about 5 weight percent urea, at least about 1 weight percent biuret based on urea, and at least about 10 weight percent of said higher molecular weight urea condensation products based on biuret.

15. The method defined in claim 1 wherein said mixture comprises at least about 5 weight percent biuret.

16. The method defined in claim 1 wherein said mixture comprises at least about 10 weight percent urea and at least about 10 weight percent biuret based on said urea, and said mixture is prepared, at least in part, by heating urea at a temperature of at least about 135° C. for a period of time sufficient to convert at least a portion of said urea to biuret.

17. The method defined in claim 1 wherein said adsorbent comprises a member selected from the group consisting of silica, alumina, magnesia, beryllia, and combinations thereof.

18. The method defined in claim 1 wherein said adsorbent comprises a member selected from the group consisting of natural and synthetic organic adsorbents comprising a polar group selected from the group consisting of hydroxyl, carbonyl, carboxyl, sulfate, phosphate, amino, amido, and combinations thereof.

19. The method defined in claim 18 wherein said adsorbent comprises a member selected from the group consisting of cellulose, acrylate copolymers, and combinations thereof.

20. A method for selectively recovering biuret from urea containing biuret and higher molecular weight urea condensation products which comprises contacting a solution or melt of said urea with a polar adsorbent having an exchange capacity no greater than about 0.1 meq./ml. under conditions sufficient to retain at least a portion of said biuret on said adsorbent, and contacting the resulting biuret-containing adsorbent with an aqueous desorbent under conditions sufficient to remove at least a portion of said biuret from said adsorbent.

21. The method defined in claim 20 wherein said higher molecular urea condensation products comprise a member selected from the group consisting of triuret, melamine, cyanuric acid, ammonium cyanurate, ammelide, methylene diurea and combinations thereof, and the resulting biuret-containing extract is substantially free of said higher molecular weight condensation products.

22. The method defined in claim 21 wherein said urea is contacted with said adsorbent as a urea melt.

23. A method for selectively recovering biuret from an aqueous urea solution containing biuret and higher molecular weight urea condensation products selected from the group consisting of triuret, melamine, cyanuric acid, ammonium cyanurate, ammelide, methylene diurea and combinations thereof, which method comprises contacting said urea solution with a polar adsorbent having an ion exchange capacity no greater than about 0.1 meq./ml. under conditions sufficient to retain at least a portion of said biuret on said adsorbent, and contacting the resulting biuret-containing adsorbent with an aqueous extractant under conditions sufficient to form an aqueous extract comprising biuret in which the relative proportion of said higher molecular weight condensation products to biuret is less than said relative proportion in said aqueous urea solution.

24. The method defined in claim 23 wherein said aqueous urea solution comprises at least about 10 weight percent urea, at least about one weight percent biuret based on urea, and at least about 10 weight percent of said higher molecular weight condensation products based on biuret, and said aqueous extract contains about 5 weight percent or less of said higher molecular weight condensation products based on biuret.

25. A method for selectively recovering biuret from a mixture comprising biuret and a member selected from the group consisting of triuret, melamine, cyanuric acid, ammonium cyanurate, ammelide, methylene diurea and combinations thereof, which comprises contacting a melt or solution of said mixture with a polar adsorbent under conditions sufficient to adsorb at least a portion of said biuret on said adsorbent, contacting the thus formed biuret-containing adsorbent with a polar desorbent under conditions sufficient to desorb at least a portion of said biuret from said adsorbent, recovering the thus formed biuret-containing extract from said adsorbent, and subsequently contacting said biuret-containing extract with a biuret-containing adsorbent under conditions sufficient to increase the biuret content of said extract.

26. The method defined in claim 25 which further comprises the step of recovering at least a portion of the biuret from said extract.

* * * * *